United States Patent
Böhner et al.

(10) Patent No.: US 10,729,523 B2
(45) Date of Patent: Aug. 4, 2020

(54) DENTAL RESTORATION AND METHOD FOR THE PRODUCTION OF A DENTAL RESTORATION

(71) Applicant: COLTÈNE/WHALEDENT AG, Altstätten (CH)

(72) Inventors: Ralf Böhner, Kriessern (CH); Cornelia Kopfmann, St. Gallen (CH); Martin Schlüter, Wangen i.A. (DE); Martin Schaufelberger, Weesen (CH)

(73) Assignee: COLTÈNE/WHALEDENT AG, Altstätten (CH)

( * ) Notice: Subject to any disclaimer, the term of this patent is extended or adjusted under 35 U.S.C. 154(b) by 0 days.

(21) Appl. No.: 15/647,725

(22) Filed: Jul. 12, 2017

(65) Prior Publication Data
US 2018/0021114 A1    Jan. 25, 2018

(30) Foreign Application Priority Data
Jul. 25, 2016    (EP) .................................. 16180992

(51) Int. Cl.
*A61C 13/00*    (2006.01)
*A61C 5/77*    (2017.01)
(Continued)

(52) U.S. Cl.
CPC ............ *A61C 13/0004* (2013.01); *A61C 5/70* (2017.02); *A61C 5/77* (2017.02); *A61C 13/0006* (2013.01);
(Continued)

(58) Field of Classification Search
CPC ......... A61C 5/70; A61C 5/77; A61C 13/0003; A61C 13/0004; A61C 13/0006;
(Continued)

(56) References Cited

U.S. PATENT DOCUMENTS 4,650,418 A    3/1987    Blair et al.
5,094,619 A *    3/1992    McLaughlin .......... A61K 6/083
106/35

(Continued)

FOREIGN PATENT DOCUMENTS

DE    196 54 055 A1    6/1998
JP    H08-112296 A    5/1996
(Continued)

OTHER PUBLICATIONS

European Search Report Corresponding to 16180992.6 dated Jan. 20, 2017.
(Continued)

*Primary Examiner* — Matthew M Nelson
(74) *Attorney, Agent, or Firm* — Davis & Bujold PLLC; Michael J. Bujold

(57) ABSTRACT

A dental restoration, a method for the production of a dental restoration and a kit. The dental restoration comprises an outer component, in particular a shell, and an inner component, in particular a core. The inner component and the outer component contain composite material. The outer component is mountable or mounted on the inner component. The inner component is designed for attachment onto a tooth preparation, in particular a tooth stump.

6 Claims, 1 Drawing Sheet

Figure 1:
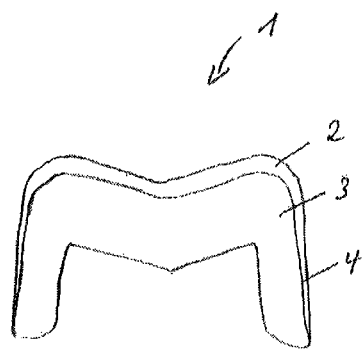

(51) Int. Cl.
*A61C 13/09* (2006.01)
*A61C 5/70* (2017.01)
*A61K 6/802* (2020.01)
*A61C 13/083* (2006.01)

(52) U.S. Cl.
CPC .......... *A61C 13/0022* (2013.01); *A61C 13/09* (2013.01); *A61K 6/802* (2020.01); *A61C 13/0003* (2013.01); *A61C 13/083* (2013.01)

(58) Field of Classification Search
CPC ... A61C 13/0022; A61C 13/083; A61C 13/09; A61K 6/0205
USPC ....................................................... 433/201.1
See application file for complete search history.

(56) References Cited

U.S. PATENT DOCUMENTS

| | | | | |
|---|---|---|---|---|
| 5,348,475 | A | * | 9/1994 | Waknine .................. A61O 5/30 433/215 |
| 2006/0257824 | A1 | | 11/2006 | Pfeiffer et al. |
| 2014/0113251 | A1 | * | 4/2014 | Schweiger ............. A61C 13/09 433/199.1 |
| 2014/0248584 | A1 | * | 9/2014 | Wolter ............... A61C 13/0004 433/202.1 |
| 2016/0008093 | A1 | | 1/2016 | Lampl |
| 2017/0300613 | A1 | * | 10/2017 | Sager ................. A61C 13/0022 |

FOREIGN PATENT DOCUMENTS

| | | |
|---|---|---|
| WO | 2006/120255 A2 | 11/2006 |
| WO | 2009/070470 A1 | 6/2009 |
| WO | 2014/153575 A1 | 10/2014 |
| WO | 2015/051095 A1 | 4/2015 |

OTHER PUBLICATIONS

Analytik Jena, "Farbemessung and Bestimmung der Transluzenz von dentine (Colour Measurement and Determination of the Translucency of Dentine)", Reference No. Feb. 2010 (To Follow).

* cited by examiner

DENTAL RESTORATION AND METHOD FOR THE PRODUCTION OF A DENTAL RESTORATION

The invention relates to a dental restoration, a method for the production of a dental restoration and a kit according to the independent claims.

In order to produce tooth-like restorations in the CAD/CAM process, multicolour blocks are used. In this, the colour changes from layer to layer or a different coloured core is used. The human tooth is made up of two layers, the relatively opaque and coloured dentine and relatively translucent and less coloured enamel. This situation is relatively difficult to emulate in a CAD/CAM process and is only approximately successful with special ready-made blocks (e.g. RealLife blocks from Vita). However, the ready-made block cannot reproduce every situation between enamel and dentine.

Multicomponent dental restorations are known. However, they are not aesthetically pleasing and are costly to manufacture. U.S. Pat. No. 4,650,418 describes dental prostheses of ceramic with an outer layer, an intermediate layer and a translucent layer.

WO 2006/120255 A2 describes dental prosthesis parts made up of a first and a second component. The production of dental prosthesis parts consisting of two types of material is possible, for example $Al_2O_3$ or ZrO for the first component and feldspar-ceramic for the second component. The first and the second components are bonded by a coloured bonding material.

The purpose of the invention is to overcome the disadvantages of the prior art. In particular, it is a purpose of the invention to provide dental restorations which are aesthetically pleasing and at the same time fulfil the high requirements which are placed on dental restorations. Further, it is a purpose of the invention to provide a process for the simplified production of dental restorations. The problems are solved by the features of the independent claims.

The invention relates to a dental restoration comprising an outer component, in particular a shell, and an inner component, in particular a core. The inner component and the outer component contain composite material. Preferably the first component and the second component consist of composite material. The outer component is mountable or mounted on the inner component. The inner component is designed for attachment onto on a tooth preparation, in particular a tooth stump or abutment. The inner component can, especially in some regions, have a lower translucency than the outer component. Preferably the translucency difference can lie in the range from 5 to 15%, particularly preferably in the range from 8 to 15%. In this way, the enamel and the dentine of the tooth are especially well emulated. Thus the dental restoration is aesthetically pleasing.

The use of an inner component and an outer component of composite material in contrast to ceramic has the advantage that the composite material of the inner component and the outer component does not expand differently, does not discolour differently, does not absorb water differently and does not have a differing refractive index. The dental restoration of composite material according to the invention is homogeneous with regard to the aforesaid properties.

The thickness of the outer component can decrease in some regions. Preferably, the thickness of the outer component decreases in the region of the dental restoration positioned cervically in the use situation. In this way, the natural tooth is realistically imitated in order to ensure an aesthetically pleasing transition between the restoration and the natural tooth substance.

The translucency of the outer component, in particular the shell, can lie in the range from 25 to 40%. The translucency of the inner component, in particular of the core, can lie in the range from 10 to 28%. In this way, an outer component and an inner component which display the aforesaid translucency differences are provided.

The inner component and the outer component can at least in some regions be glued together in such a way that a cohesive bond is formed from the inner component and the outer component. In fracture tests with the bond a cohesive fracture occurs, that is cohesively in the material of the inner component or the outer component and not in the adhesive joint or the glued surfaces. The cohesive fracture can take place in the inner component, in the outer component and in the adhesive. Of course, the fracture can also take place through two of the three aforesaid components. The dental restoration according to the invention is thus formed as a cohesive bond.

Preferred adhesives for the gluing of the inner component and the outer component are acrylic-containing adhesives. These can have a similar composition with regard to the composite composition of the inner component and the outer component. Different compositions are of course also possible.

A further aspect of the invention relates to a process for the production of a dental restoration, in particular as explained above. The process comprises the step of the provision of CAD/CAM data of a tooth preparation, in particular a tooth stump, for the production of an individualized restoration. In this way, the individual features of tooth preparation are taken into account in the process and an individual restoration is made possible. The process comprises the step of producing an outer component, in particular a shell, from a first composite block or from a first region of a composite block comprising at least two regions and producing an inner component, in particular a core, from a second composite block or from a second region of the composite block comprising at least two regions.

The first composite block and the second composite block or the first region and the second region of the composite block comprising two regions preferably differ in the composition of their composite material. In this way, the first and the second composite block or the first region and the second region of the composite block have at least one different property.

The translucency of the second composite block or of the second region of the composite block can, particularly in some regions, be lower than the translucency of the first composite block or of the first region of the composite block. Preferably the translucency difference is in the range from 5 to 15%, particularly preferably in the range from 8 to 15%. Optionally, the outer component is mounted on the inner component. The inner component is designed for attachment onto the tooth preparation, in particular the tooth stump or abutment. In this way, the outer components and the inner component of a dental restoration are produced individualized; at the same time, translucencies and colour intensities are taken into account, which results in an excellent aesthetic effect.

Here and below, a composite block is understood to mean a block produced from composite material, which essentially has the shape of a rectangular block, a cube or a disc. In principle, other geometrical shapes are also possible.

The composite material of the composite block or blocks consists of an organic matrix and a filler. Suitable composite materials comprise an organic plastic matrix (organic phase), which is mixed with an inorganic, in particular solid, filler (inorganic phase). Advantageously, the organic plastic matrix comprises at least one methyl acrylate and/or the inorganic filler at least one glass. As the glass, a barium glass and/or a strontium glass are preferably used.

Further preferred inorganic fillers are amorphous, e.g. spherical, materials for example based on mixed oxides of $SiO_2$, $ZrO_2$ and/or $TiO_2$, microfine fillers, such as pyrogenic silicic acid or precipitated silicic acid and macro- (particle size from about 5 µm to about 200 µm) or micro-fillers (particle size from about 0.5 µm to about 5 µm), such as quartz (silicates, sands), glass ceramics (e.g. barium-aluminium glass) or glass powder with an average particle size from 0.5 µm to 5 µm and radiopaque fillers, such as ytterbium trifluoride. Likewise, the filler can also comprise so-called microfiller complexes such as for example hybrid composites and nanoparticles (nano-hybrid composites). Furthermore, glass fibres, polyamides or carbon fibres can in principle also be used as fillers. The surface of the filler is as a rule silanized in order to enable bonding with the organic matrix.

Further suitable polymerizable mono- or multifunctional monomers of the organic phase are mono(meth)acrylates, such as methyl, ethyl, butyl, benzyl, furfuryl or phenyl (meth)acrylate, and multifunctional acrylates and methacrylates such as for example bisphenol A di(meth)acrylate, bisphenol A glycidyl methacrylate (known as "bis GMA", which is an addition product of methacrylic acid and bisphenol A diglycidyl ether), UDMA (an addition product of 2-hydroxyethyl methacrylate and 2,2,4-hexamethylene diisocyanate), di-, tri- and tetraethylene glycol di(meth)acrylate (such as for example TEGDMA), decanediol di(meth) acrylate, trimethylolpropane tri(meth)acrylate, pentaerythritol tetra(meth)acrylate and butanediol di(meth) acrylate, 1,10-decandiol di(meth)acrylate or 1,12-dodecandiol di(meth)acrylate. Organic phases comprising methacrylate-modified polysiloxanes are also known.

The composite material of the composite blocks can contain >40 wt. % of a filler, in the sense of a filler or a mixture of fillers. Here in particular a composition ratio is provided which represents one single component or compositions of single components. The filler or fillers can be singular, in the sense of isolated fillers, but also be present agglomerated or as clusters. Agglomerates are in general understood to mean more or less consolidated accumulations of previously loose constituents into a solid bond. In process technology, agglomerates are for example obtained by granulation, coagulation or sintering. The clusters here can be mechanically or chemically bonded. The aforesaid >40 wt. % of filler can contain 0 to 100 wt. % dental glass with an average particle size from 0.1 to 5 µm (obtainable for example from Schott), 0 to 100 wt. % chips of organic matrix and an organic filler with an average particle size from 1 to 30 µm. Here the chips correspond to a ground composite material. Furthermore, the composition comprises 0 to 100 wt. % of inorganic filler produced in the sol-gel process with an average particle size from 0.1 to 5 µm and 0 to 100 wt. % of an in particular pyrogenic silicic acid with an average particle size from 0.002 to 0.25 µm. In this manner, composite blocks which meet the requirements in the dental field, for example as regards abrasion properties, compressive hardness and durability, are provided.

The dimensions of the composite blocks can have a breadth in the range from 0.5 to 5 cm, in particular 1 to 3 cm, and/or a base area in the range from 0.25 to 25 $cm^2$, in particular 1 to 9 $cm^2$. Dimensions of 12 cm×3 cm, in particular 10 cm×2.5 cm, can also be provided. In this manner, components of the dental restorations of very different sizes can be produced from the composite block.

The translucency of the first composite block or of the first region of the composite block can lie in the range from 25 to 40%. The translucency of the second composite block or of the second region of the composite block can lie in the range from 10 to 28%. In this way, an outer component and an inner component which display the aforesaid translucency differences are provided.

The inner component and the outer component can at least in some regions be glued together in such a way that a cohesive bond is formed; this especially in some regions in the contact region which is formed between the inner component and the outer component. Alternatively, the inner component and the outer component can be glued together in the whole contact region between the inner component and the outer component. Alternatively, the first region or the second region of the composite block can be glued together at least in some regions or in the whole contact region in such a way that a cohesive bond is formed. In this way, a cohesive bond is obtained which has the advantages as regards the fracture behaviour already previously explained. Particularly preferable adhesives are the previously mentioned acrylic-containing adhesives.

A further aspect of the invention relates to a kit for the production of dental restorations, in particular as explained above, comprising an outer component, in particular a shell, and an inner component, in particular a core. The kit contains several first composite blocks for the production of outer components. Here the translucencies of the first composite blocks are different, with the translucencies in particular lying in the range from 25 to 40%. The kit further contains several second composite blocks for the production of inner components. The translucencies of the second composite blocks are different, with the translucencies in particular lying in the range from 10 to 28%.

Alternatively, the kit contains several composite blocks, which have a first region for the production of outer components, in particular shells, and a second region for the production of inner components, in particular cores, wherein the translucencies of the first regions are different and/or the translucencies of the second regions are different. The translucencies of the first regions lie in particular in the range from 25 to 40%, and/or the translucencies of the second region lie in particular in the range from 10 to 28%.

Optionally the kit contains instructions for use. The kit provides the dentist or the dental technical with a wide selection of different composite blocks for the production of the inner component and the outer component for a dental restoration, in particular an individualized dental restoration. In this way, a combination of composite blocks for the production of the inner component and the outer component can be selected and components with the aforesaid advantageous translucency differences produced.

The kit can contain an acrylic-containing adhesive. Here the acrylic-containing adhesive can preferably have a similar composite composition to the first composite block and the second composite block.

A further aspect of the invention relates to a composite block having at least one first region for the production of an outer component, in particular a shell, and a second region for the production of an inner component, in particular a core, of a dental restoration. The first region and the second region consist of composite material. Thus a composite block is provided from which dental restorations which have the advantages of composite materials in comparison to ceramic explained above can be produced.

The composite block can also have three or more regions. If the regions differ in a property (e.g. composite composition), further components of a dental restoration can be manufactured from the composite block.

The translucencies of the first region and the second region of the composite block are preferably different. In this way, components with different translucencies can be produced from the regions of the composite block.

The first region can, especially in some regions, have a lower translucency than the second region. In this way, from the first region for example an outer component, in particular a shell, and from the second region for example an inner component, in particular a core, of a dental restoration which has an advantageous aesthetic effect owing to the different translucencies of their components can be manufactured.

The translucency difference of the first region and the second region can lie in the range from 5 to 15%, preferably 8 to 15%.

The translucency of the second region preferably lies in the range from 10 to 28% and/or the translucency of the first region preferably lies in the range from 25 to 40%. In this manner, a composite block is provided from which components which have the advantages explained above as regards the aesthetic effect can be produced.

The first region and the second region of the composite block form a contact region. This contact region between the first region and the second region can be flat or curved.

The contact surface of the first region for contacting with the second region in the contact region between the first region and the second region can be an inside taper. In this way, a dental restoration can be produced more simply, since a dental restoration made of two components can be produced along inside taper of the first region and the corresponding cone of the second region.

Furthermore, the first region and the second region of the composite block can at least in some regions be glued together in such a way that a cohesive bond is formed. A dental restoration produced from the two regions, wherein the gluing of the regions is retained in the restoration, has the advantageous cohesive fracture properties previously explained.

Translucency Measurement

The measurement was made on a UV/Vis spectrophotometer (Specord 210 from AnalytikJena) according to measurement instructions adapted from AnalytikJena, Farbemessung and Bestimmung der Transluzenz von dentine [Colour measurement and determination of the translucency of dentine], Reference No.: 02/2010.

With the integrating sphere, transmission and remission measurements of dispersive solid and liquid samples and of powder samples are possible. For the determination of the translucency of dental materials, reflection spectra in the VIS region, which were evaluated by means of colour software, were recorded.

As the reference, the Spectralon insert of the sphere was used. For the determination of the translucency a small plate (1 mm) was used, which was measured each time with no background (black standard) and with a white standard as the background. The white standard was also used as a reference here.

The remission spectra were recorded with setting of the illuminant D65 and an observer from 10°. The following parameter settings were used:

| | |
|---|---|
| Instrument | Specord 210 |
| Accessories | Integrating sphere |
| Display | Transmission |
| Correction | Reference |
| Slit | 4 nm |
| Bulb change | 320 nm |
| Measurement mode | Step operation |
| Range [nm] | 380-780 nm |
| Step width [nm] | 1 nm |
| Integration time [s] | 0.2 s |

In addition, to check the accuracy of the method three certified colour standards were measured.

The translucency T (in %) was then calculated from the following formula:

$$\% \ T = ((L_{white} - L_{black})/L_{white}) \times 100\%$$

The invention is explained in more detail on the basis of practical examples given by way of example.

Figure 2:
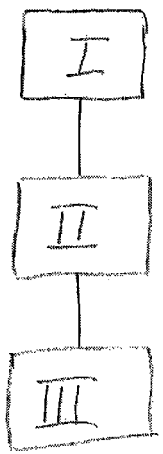
Figure 3:
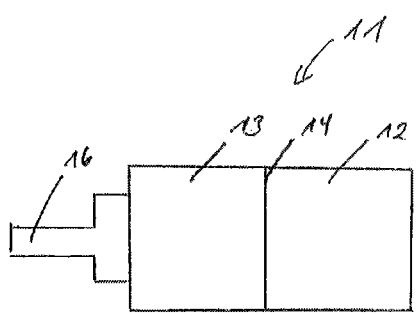
Figure 4:
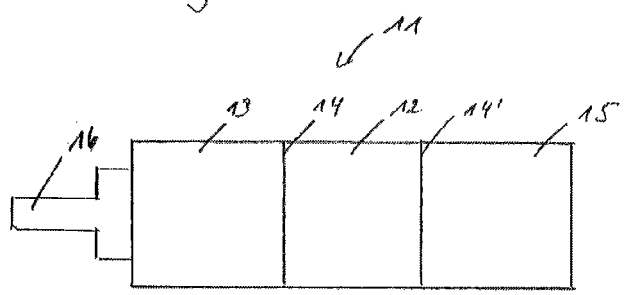

FIG. 1: shows a diagrammatic cross-section representation of one embodiment of the restoration according to the invention, FIG. 2: a flow diagram of one embodiment of the method according to the invention, FIG. 3: a diagrammatic representation of a composite block having two regions, and FIG. 4: a diagrammatic representation of a composite block having three regions.

FIG. 1 shows a dental restoration 1 comprising a shell 2 and a core 3. The shell 2 and the core 3 are made of composite material. The shell 2 is glued together with the core 3 in the contact region 4 between the shell 2 and the core 3. As the adhesive, an acrylic-containing adhesive which has a similar composite composition to the shell 2 and the core 3 is used. The gluing in the contact region 4 results in a bond with cohesive fracture properties. In fracture tests, the bond does not fracture at the gluing site or gluing surface but rather in the material of the shell 2 or the core 3. The bond of shell 2 and core 3 forms a cohesive bond. The core 3 is designed such that it can be attached onto a tooth preparation. The core 3 has a lower translucency than the shell 2. The translucency difference between shell 2 and core 3 lies in the range from 5 to 15%.

By way of example, the shell 2 has a translucency of 30% and the core a translucency of 20%.

The thickness of the shell 2 decreases in the regions of the dental restoration 1 positioned cervically in the use situation. The shell 2 is thus designed tapering. In this way, the natural tooth is realistically imitated in order to ensure an aesthetically pleasing transition between the restoration and the natural tooth substance.

FIG. 2 shows a flow diagram of one embodiment of the process according to the invention. The process relates to the production of a dental restoration. The process comprises the step I of the provision of CAD/CAM data of a tooth preparation for the production of an individualized restoration. In this way, the individual features of a tooth preparation are taken into account in the process and an individual restoration is made possible.

The process comprises the step II, wherein a shell (see shell 2 in FIG. 1) is produced from a first composite block and a core (see core 3 in FIG. 1) from a second composite block. This takes place in a CAD/CAM process. The translucency of the second composite block for the production of the core is lower than the translucency of the first composite block for the production of the shell. The translucency difference between shell and core is in the range from 5 to 15%. The core is designed for attachment onto the tooth preparation.

The process further comprises the step III, wherein the shell and the core are glued together. The gluing results in the advantageous properties of the restoration as explained for FIG. 1 as regards a cohesive bond. Furthermore, in this way the shell and the core of a dental restoration are produced individualized; at the same time translucencies and colour intensities are taken into account, which results in an excellent aesthetic effect.

FIG. 3 shows a composite block 11 having a first region 12 and a second region 13. The first region 12 and the second region 13 are bonded together in the contact region 14. The regions 12 and 13 can also be positioned the other way round.

The composite material of the first region 12 differs from the composite material of the second region 13 in at least one property. Here the composite material of the first region 12 has a lower translucency than the composite material of the region 13. From the region 13, a core of an individual dental restoration can for example firstly be produced in a CAD/CAM process. For this, the composite block 11 is clamped into a suitable device by means of a support 16. Without a further change in clamping, a shell of the individual dental restoration can be produced from the first region 12. The use of the composite block 11 in a CAD/CAM process for the production of an individual dental restoration optimizes the production process, since the composite block 11 provides the materials for a shell and a core.

FIG. 4 shows a composite block 11. The explanations on FIG. 4 apply equally. The composite block 11 of FIG. 4 has a third region 15, which is connected to the first region 12 via a contact region 14'. In this way, the composite block 11 provides a third composite material which differs in at least one property from the composite materials of regions 12 and 13. In this way, a further component can be made from the composite block 11 in a CAD/CAM process without a clamping change, say a clamping of a further composite block, being necessary.

The invention claimed is:

1. A method for production of a dental restoration (1) having an outer component and an inner component, comprising the steps of:
    providing CAD/CAM data for a tooth preparation;
    producing the outer component from a first composite block or from a first region of a composite block comprising at least two regions and producing the inner component from a second composite block or from a second region of the composite block comprising at least two regions, wherein said composite block or blocks consist of an organic matrix and a filler, wherein said outer component is mountable or mounted on said inner component; and
    designing said inner component for attachment onto a tooth preparation.

2. The method according to claim 1, comprising the step of mounting said outer component on said inner component.

3. The method according to claim 1, wherein said tooth preparation is a tooth stump for the production of an individualized restoration.

4. The method according to claim 1, wherein a translucency of at least some region of said second composite block or of said second region of said composite block is lower than a translucency of said first composite block or of said first region of said composite block and/or a translucency difference of said first and said second composite block or of said first region and said second region of said composite block lies in a range from 5 to 15%.

5. The method according to claim 4, wherein the translucency of said first composite block or of said first region of said composite block lies in a range from 25 to 40% and/or the translucency of said second composite block or said second region of said composite block lies in a range from 10 to 28%.

6. The method according to claim 1, wherein said inner component and said outer component or said first region and said second region of said composite block are glued together, at least in some regions, in such a way in such a way that a cohesive bond is formed.

* * * * *